United States Patent [19]

Asher

[11] Patent Number: 5,427,686
[45] Date of Patent: Jun. 27, 1995

[54] PROCESS FOR SEPARATING MATERIAL FROM MIXTURE USING DISPLACEMENT CHROMATOGRAPHY

[75] Inventor: William J. Asher, Half Moon Bay, Calif.

[73] Assignee: SRI International, Menlo Park, Calif.

[21] Appl. No.: 223,165

[22] Filed: Apr. 5, 1994

[51] Int. Cl.$^6$ .............................................. B01D 15/08
[52] U.S. Cl. .................................. 210/635; 210/656; 210/659; 210/198.2
[58] Field of Search ...................... 210/635, 656, 198.2, 210/659; 436/161

[56] References Cited

U.S. PATENT DOCUMENTS

| | | | |
|---|---|---|---|
| 3,920,398 | 11/1975 | Small | 210/656 |
| 3,925,019 | 12/1975 | Small | 210/656 |
| 3,971,842 | 7/1976 | Ewbank | 210/267 |
| 4,394,353 | 7/1983 | Miyake | 210/681 |
| 4,599,175 | 7/1986 | Yamamizu | 210/635 |
| 4,600,566 | 7/1986 | Fujine | 423/181 |
| 4,915,843 | 4/1990 | Taniguchi et al. | 210/635 |
| 5,028,696 | 7/1991 | Torres | 530/387 |

OTHER PUBLICATIONS

Cramer, Steven M., et al., "Recent Advances in the Theory and Practice of Displacement Chromatography," *Separation and Purification Methods*, vol. 19, No. 1, 1990, pp. 31–91.

Horváth, Csaba, "Displacement Chromatography: Yesterday, Today and Tomorrow," in *The Science of Chromatography*, edited by Fabrizio Bruner, Amsterdam: Elsevier, 1985, pp. 179–203.

*Primary Examiner*—Ernest G. Therkorn
*Attorney, Agent, or Firm*—John P. Taylor

[57] ABSTRACT

A separation process is described for separating a known material from a mixture of materials (which may contain unknown materials) using displacement chromatography. The process comprises passing a mixture of materials, including a known material to be recovered, dissolved in a liquid carrier, if necessary, through a first packed column and into a second packed column until all of the known material has passed through the first column and has been loaded onto the stationary phase packing in the second column. A displacement agent, capable of being more strongly bound on the stationary phase packing in the second column than the known material, is then passed through the second column to displace from that column all of the materials in the mixture less strongly bound than the known material, and then to displace the known material from the second column. The columns are then regenerated, preferably by passing a carrier directly through column 2 (in the forward direction of flow) and then passing the effluent from column 2 through column 1 in a reverse direction. The flow through column 2 is continued until all of the displacement agent has been removed from column 2. In one embodiment, a solvent is also counter flushed through the first column to dissolve any precipitates therein.

31 Claims, 5 Drawing Sheets

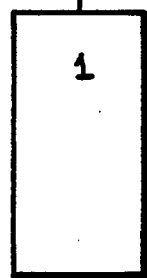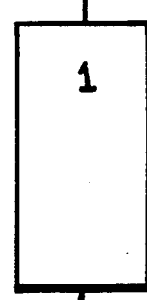
FIG. 3  FIG. 4

PROCESS FOR SEPARATING MATERIAL FROM MIXTURE USING DISPLACEMENT CHROMATOGRAPHY

BACKGROUND OF THE INVENTION

1. Field of the Invention

This invention relates to displacement chromatography. More particularly, this invention relates to a process for separating a known material from a mixture of materials using displacement chromatography.

2. Description of the Related Art

In the practice of displacement chromatography, a mixture of several materials, dissolved in a carrier, are loaded onto a stationary phase material in a chromatography column. Then a displacement agent, comprising a material capable of being more strongly bound to the stationary phase material than the particular material of interest in the mixture, and usually capable of being more strongly bound than any of the other materials in the mixture, is fed through the column to displace the already bound materials, with the most weakly bound material coming off the column first by being displaced by the next most weakly bound material.

The feasibility of this separation method has been demonstrated using known mixtures of materials, wherein a displacement agent may be selected which is more strongly bound to the stationary phase than any of the other materials, by virtue of being able to intelligently select such a displacement agent based on the prior knowledge of the other materials in the mixture. However, problems arose in the past when this separation technique was applied by others to a situation wherein a known material was to be separated from an unknown mixture, i.e., a mixture which might contain unknown materials. In such a situation, it was difficult, and sometimes impossible, to preselect a displacement agent capable of displacing all of the materials in the mixture, when that mixture did contain unknow materials, and in particular when some of such unknown materials were more strongly bounded to the stationary phase than the displacement agent selected.

I believe that the principal reason why displacement chromatography has never achieved commercial success is the failure of others to recognize the importance of the presence of these unknown materials in commercial solutions or materials, as opposed to artificial or model laboratory preparations.

Even when all of the components in the mixture are known, but some are substantially more strongly held than the desired component, it has become accepted by those skilled in the art that to satisfactorily practice displacement chromatography, one must use a displacement agent capable of being more strongly bound to the stationary phase than any of the materials in the mixture to be separated.

However, this can diminish the value of displacement chromatography as a separation tool for many mixtures, because one must first conduct tests to determine the most strongly bound material in the mixture, then determine whether or not a stronger displacement agent is available, and then determine the economics of using such a strong displacement agent.

It has also been found that in practical commercial mixtures, there are present components in small concentrations which frequently elude analysis, but are more strongly bound to the stationary phase than the displacement agent selected to be more strongly bound than the components which could be found by the analysis. The presence of this small concentration of materials more strongly bound than the selected displacement agent prevents or interferes with successful displacement chromatography.

It would, therefore, be desirable to provide a process for practicing displacement chromatography without requiring the use of a displacing agent more strongly bound to the stationary phase than any component in a feed mixture.

SUMMARY OF THE INVENTION

It is, therefore, an object of this invention to provide a process for separating a desired known material from a mixture of materials, which may contain unknown materials, using displacement chromatography.

The invention comprises passing a mixture of materials dissolved, if necessary, in a liquid carrier, including a desired known material, through a first packed column and into a second packed column in a manner limiting the quantities of materials more strongly held than the desired known material on the first column from passing from the first column and onto the stationary phase packing in the second column. A displacement agent, capable of being more strongly bound on the stationary phase packing in the second column than any of the materials on that column, is then passed through the second column to displace from that column all materials present thereon, including materials less strongly bound than the desired known material and then the desired known material. The columns are then regenerated, preferably by passing a career directly through column 2 (in the forward direction of flow) and then passing the effluent from column 2 through column 1 in a reverse direction. The flow through column 2 is continued until substantially all of the displacement agent has been removed from column 2. In one embodiment, a solvent is also counter flushed through the first column to dissolve any precipitates therein.

BRIEF DESCRIPTION OF THE DRAWINGS

FIG. 3 is a diagrammatic depiction of the regeneration step of the process.

FIG. 4 is a diagrammatic depiction of an alternate embodiment of the process showing a washing step with a solvent being carried out in the first column to dissolve precipitates while the displacement step of the process is being carried out in the second column.

DETAILED DESCRIPTION OF THE INVENTION

Figure 1:
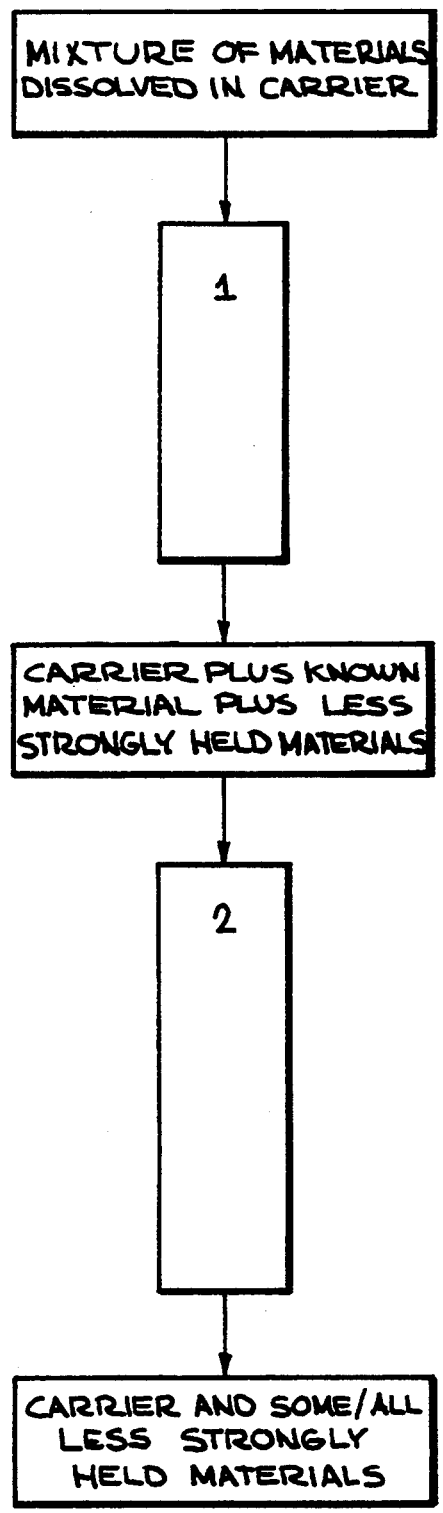
FIG. 1 is a diagrammatic depiction of the loading step of the process.

The process of the invention comprises passing an unknown mixture of materials, dissolved in a liquid carrier (if not already in a liquid state), through a first packed column and into a second packed column in a manner limiting the quantities of materials, held more strongly than a desired known material in the mixture, passing through the first column and onto the stationary phase packing in the second column. The term "desired known material" refers to the material sought to be recovered from the mixture of materials, which mixture may contain unknown materials.

The limiting of the quantities of materials, held more strongly than the desired known material, passing through the first column and onto the stationary phase packing in the second column, can be done by either of two methods. The first and preferred method is to either stop the flows through the columns when materials more strongly held than the desired known material start appearing in the effluent from the first column or to stop the flow before any materials more strongly held than the desired materials exit the first column. The point at which the flow is stopped (when the flow is stopped prior to detection in the effluent of materials more strongly held than the desired known material) may be empirically determined, as will be explained later.

In the second, but less preferred method, for either stopping point, carrier alone (i.e., carrier without feed material therein) may then be substituted for the feed in carrier and is flowed through the two columns. This elutes the more weakly held materials from column 1 into column 2. This eluting flow is then stopped before any substantial amounts of materials more strongly held than the one or more desired known materials enter column 2.

Regardless of which of the above methods is used, a displacement agent, capable of being more strongly bound on the stationary phase packing in the second column than any material sorbed on the second column, including the desired known material, is then passed into the second column to displace from that column all material present thereon. The displacement agent first causes displacment from the second column of materials less strongly bound than the desired known material; then causes displacment from the column of the desired known material; and finally causes displacment from the second column of any material more strongly bound thereto than the desired known material. By causing the removal, in the first column, of substantially all of the unknown materials in the mixture more strongly bound than the one or more desired known materials to be recovered, the subsequent displacement chromatography separation carried out in the second column can be carried out using a displacement agent which is more strongly bound to the stationary phase than the desired known material previously loaded onto the stationary phase packing material in the second column (as well as any other materials bound in the second column).

It should be noted, in this regard, however, that it may be impossible, from a practical position, to prevent all materials more strongly held than the desired known material from passing out of the first column and onto the second column. However, the number of such materials will usually not number more than one or two, and such materials can be identified, e.g., by elution chromatography analysis of samples from a previous run under identical conditions, and a displacement agent can then be selected which will be more strongly held than even such materials so that all of the materials sorbed in the second column will be removed by the selected displacement agent.

After the displacement step, the columns are regenerated. The columns may preferably be regenerated by passing either the same or a different carrier, preferably the same carrier, directly through column 2 (in the forward direction of flow) and then passing the effluent from column 2 through column 1 in a reverse direction. The flow through column 2 is continued until all of the displacement agent has been removed from column 2. In one embodiment, a solvent is also counter flushed through the first column to dissolve any precipitates therein. This is preferably done prior to the regeneration step.

The Column and Stationary Phase Packing Material

In accordance with the invention virtually any size column may be used for either the first or second columns. However, for a given volume of a given mixture of unknown materials, the sorption capacity of the first column should be the same or preferably greater than the total quantity of materials in the mixture which are more strongly bound to the stationary phase packing than the desired known material which is to be separated from the unknown mixture. Otherwise too much of the more strongly bound material will pass through the first column (once it is loaded to capacity) which would defeat the object of the invention, which is to separate out from the desired known material substantially all of the more strongly bound unknown materials prior to the displacement step carried out in the second column. For a given liquid, this required minimum sorption capacity of the first column may be determined empirically, for example, by initially using an oversized column and then gradually reducing the volume of the packed bed.

Similarly, for such a given volume of a given mixture of unknown materials, the sorption capacity of the second column must be at least the same as, and preferably at least twice, the quantity of the desired known material, so that all of the desired known material may be loaded onto the second column prior to commencement of flow of the displacement agent through the second column. It should be noted, however, that the sorption capacity of the second column need not be large enough to also permit loading of all of the less strongly bound materials as well as the desired known material at the same time, since separation of the less strongly held materials, by their displacement from the second column by the desired known material, during loading of the desired known material into the second column, provides a satisfactory separation.

To take full advantage of the process of this invention, the sorption capacity of the second column should be large enough to allow a fully developed train of concentrated bands of the components remaining on this second column in the subsequent displacement step. Generally, the ratio of the quantity of desired known material to be recovered to the volume of the stationary phase in the second column is between 5 and 50 times greater than when the same stationary phase is used to analyze the desired known material using elution chromatography. However, this ratio of quantity of desired known material to volume of stationary phase may be as low as 1 and as high as 250.

A typical column size for an industrial separation, for example, may range from about 0.45 centimeters (cm) to about 2000 cm in diameter and from about 5 cm to about 2000 cm in length. The overall sorption capacity of column 1 versus column 2 will depend upon the relative concentrations of materials in the unknown mixture more strongly bound to the stationary phase than the desired known material versus the concentration of desired known material in the unknown mixture. If the concentration of materials in the mixture which are more strongly bound to the stationary phase than the desired known material exceeds more than twice the total concentration of the desired known material in the mixture, then the first column should be larger in sorption capacity than the second column. This relative capacity of the various materials can also be empirically determined in advance by conventional analytical means, such as, for example, using conventional elution chromatography with the same stationary phase and carrier to be subsequently used in the displacement chromatography process of this invention.

The packing material comprising the stationary phase to be loaded into the columns may comprise virtually any stationary phase material capable of permitting selective bonding of materials thereon, including strong or weak cationic and anionic exchange materials, and adsorption materials such as silica or alumina. Also included are bonded phase chromatographic stationary phases which frequently have an organic molecule with 4–18 carbon atoms chemically bound to a rigid support such as silica. Both the native and modified cyclodextrans on support can be used, as can all of the stationary phases being developed for the separation of chiral compounds. In general, it can be said that the process of the invention can be used with all stationary phases used in chromatography except those which separate by excluding molecules too large to enter the pores of the stationary phase.

It should be further noted that the stationary phase packing material used in column 1 preferably will be the same material as used in column 2. However, in some circumstances, it may be desirable or necessary to use separate, i.e. different, packing materials in column 1 and column 2 and it will be understood that it is within the scope of the invention so to do.

The size of the individual particles of the stationary phase packing materials is also not important, although a minimum average particle size diameter of at least about 5 micrometers ($\mu$m) is desirable from a standpoint of minimum pressure drop through the columns (too small a particle size can impede the flow of the liquid through the bed). A maximum average particle size diameter (for a non-porous particle) of not greater than about 1000 micrometers ($\mu$m) is also desirable from a standpoint of efficiency (larger particle sizes will have too small an area for a given volume of packing materials to be efficient for bonding of the materials to be separated). There is also an upper diameter limit with newer porous particles which include through pores for additional area such as the Poros ® packing by PerSeptive Biosystems. Diameters of less than 3 millimeter (mm) are preferred for such types of particles.

The Feed Mixture and Carrier

The process of the invention may be used to separate out a desired known material from any unknown mixture of materials capable of being dissolved, if necessary, in a liquid carrier which may be used with any of the above stationary phase materials. Examples of a known material in a mixture of materials (which could also contain unknown materials) might include, for example, separation of a known protein or an amino acid (or other biochemical material) present in a mixture of biochemicals: such as a body fluid, e.g., blood plasma; a fermentation broth; or a lysate from cells modified by DNA methods.

The liquid carrier used to dissolve the materials (when the mixture is not already in liquid form), and to load the materials onto the stationary phase material in the columns, may comprise virtually any liquid which is a solvent for the solid materials in the mixture, but not a solvent for the stationary phase packing material. Such carriers include, by way of illustration and not of limitation, water and aqueous solutions; alcohols, including methanol, ethanol, isopropyl alcohol, and butanol; alkanes both straight chain and cyclic) including pentane, hexane, heptane, octane, and cyclohexane; aldehydes and ketones such as formaldehyde, acetaldehyde, acetone, and methylethylketone (MEK); aromatics such as benzene, toluene, and naphthalene; and aromatic heterocyclics such as tetrahydrofuran, and solvents containing various heteroatoms such as dimethylsulfoxide, acetonitrile, and dioxane.

The Displacement Agent

The displacement agent may comprise any material which is more strongly held by, or capable of being bonded to, the stationary phase packing material in the second column than any material already sorbed on the second column. Examples of typical displacement materials include butanol, n-heptanol, tetrabutylammonium bromide, and octadecyldimethylammonium chloride. As examples of displacement agents useful with particular known steroid materials to be separated from unknown mixtures; 4-pentene-1-ol may be used as the displacement agent when separating cholesta-5,7,24-triene-3-ol from a mixture using a silver ion-loaded stationary phase; and benzyltributylammonium chloride may be used as the displacement agent when separating histidine and argine from a mixture, using a cation exchange stationary phase.

The Loading Step (First Method)

Referring now to FIG. 1, a fixed volume of a mixture of materials present in a liquid carrier is first passed through column 1, with the effluent emerging from column 1 being fed into column 2. This effluent from column 1 is monitored for content of materials more strongly held by the stationary phase than the desired known material, and in particular for the first material which is more strongly held than the desired known material. Identification of this particular material can already have been determined from a previous test run. When the presence of this first material more strongly held to the stationary phase than the desired known material is detected in the carrier fluid exiting column 1, the flow into (and out of) column 1 is shut off.

At this point substantially all materials in the mixture which are more strongly bound to the stationary phase in column 1 than the desired known material are loaded on column 1 (but not on column 2), with only a minor amount of the first material more strongly held than the desired known material present on the stationary phase in column 2 as the most strongly held material loaded on column 2. Recovery of the desired known material by displacement from column 2 may now be carried out as will be explained below.

By use of the term "substantially" to describe the amount of such more strongly bound materials which are loaded on the first column, and the term "minor" to describe the mount of such more strongly bound materials which may be present on the stationary phase in the second column, is meant that at least about 90 wt. % of the total amount of such more strongly bound materials originally present in the liquid feed mixture are separated out by the first column and less than 10 wt. % of the total amount of such more strongly bound materials originally present in the liquid feed mixture are present on the second column. Thus, if the original concentration of such more strongly bound materials in the liquid feed mixture is 100 mg/liter and one liter of such feed mixture is passed through the first column, with the effluent then passed to the second column, more than 90 mg of such more strongly held materials will be bound to the stationary phase in the first column, and less than 10 mg of such materials will pass through the first column and be loaded onto the second column.

The Loading Step (Second Method)

As an alternative to the just described loading step, the loading step may be separated into two phases. This alterative is particularly advantageous when a different stationary phase is used in the second column from the stationary phase used in the first column, and the stationary phase in the first column is less strongly bound to the desired known material than the stationary phase in the second column. In this method, the mixture of materials in a carrier are passed through the first column (as in the first method). However, in this method when the quantity of the desired known material selected for ultimate loading on column 2 has been passed through column 1 (which is connected to column 2 as shown in FIG. 1), this flow is stopped. Alternatively, the flow may be stopped just before the first more strongly held material than the desired known material appears in the effluent from column 1. Either of these stopping points may be empirically determined from previous runs of the same feed carrier through column 1, i.e. through the same stationary phase in the same volume in an identical column.

In either case, after stopping the flow of the feed carrier into column 1, an eluting carrier without feed material therein (either the same or a different carrier) is fed through column 1 and into column 2 to elute from column 1 materials held thereon from the flow of the feed carrier therethrough. The flow of this carrier through column 1 is then continued until the concentration of the desired known material exiting column 1 has dropped to some predetermined low concentration, which preferably is about 1% of the concentration of the desired known material in the original feed carrier, to provide for maximum subsequent recovery of the desired known material from column 2.

The Displacement Step

Figure 2:
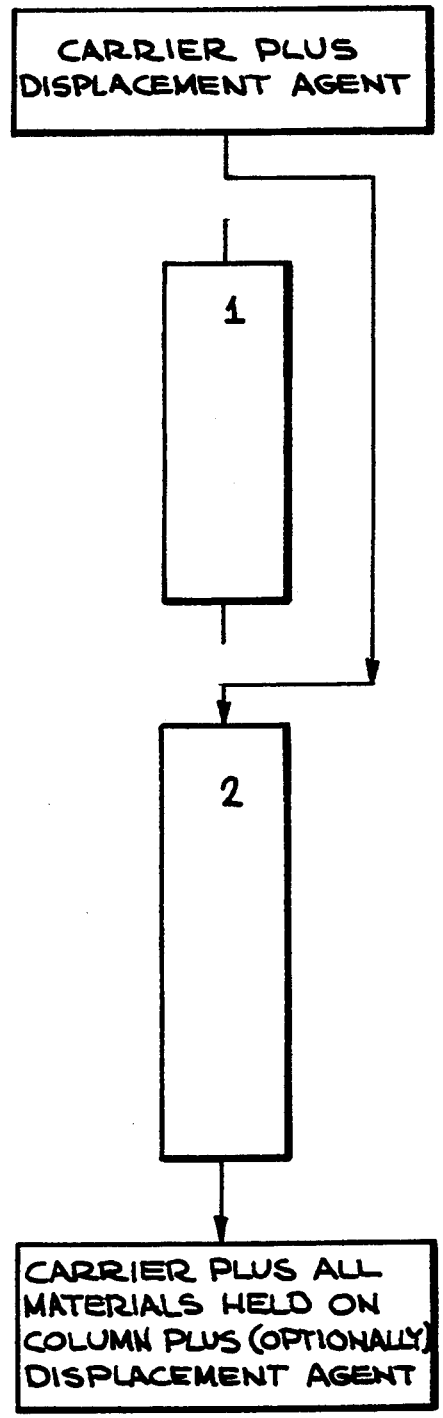
FIG. 2 is a diagrammatic depiction of the displacement step of the process.

A displacement agent which is more strongly bound to the stationary phase than any material held on the stationary phase in the second column, including the desired known material to be recovered, is then selected to displace all materials loaded on column 2. This displacement agent, in a liquid carrier if needed, is then passed directly into column 2, as shown in FIG. 2, to displace the desired known material therefrom, as well as all other materials held thereon. If the capacity of column 2 exceeds the amount of the desired known material loaded thereon, other less strongly held materials will be first displaced by the desired known material being moved through the column and such less strongly held materials will appear in the effluent from column 2. This portion of the column 2 effluent may be discarded or otherwise processed, if desired, to recover the carrier, etc. The carrier fluid carrying the desired known material will then be collected as it passes from column 2, and the flow of displacement liquid will be continued into and through column 2 until any other materials held thereon are also displaced, and displacement agent begins to appear in the effluent.

Depending upon the desired purity of the desired known material being collected, the shut off point for collecting product, i.e. the desired known material, may occur when as little as 5 ppm of the displacement agent begins to appear with the desired known material in the carrier effluent from the second column, depending upon the desired purity. At this time the flow of displacement agent and carrier through column 2 may be shut off. The desired known material may then be separated, if desired, from the liquid carrier using any conventional technique which forms no part of the present invention. When the known material is separated from the liquid carrier, such separated carrier may then be used in the regeneration step to be described below, which will improve the overall economics of the process.

As previously discussed, in many practical instances, a small quantity of a material more strongly held than the desired known material to be recovered will also be carried into the second column, usually the first more strongly held material, as discussed above in connection with the first loading method. This will occur in instances where some of the first component more strongly held than the desired known material leaves the first column before the flow into the second column is stopped. In such instances, the particular displacement agent selected should be more strongly held to the stationary phase in column 2 than this material, i.e., be more strongly held to the stationary phase in column 2 than any material held thereon. This will avoid the previously discussed prior art problem wherein certain unknowns in a mixture eluded analysis and were not, therefore, taken into account when selecting a proper displacement agent.

By selecting a displacement agent more strongly held than any materials held to the stationary phase in column 2, any such more strongly held material or materials on the stationary phase in column 2 will then be displaced and pushed through the column in a small band behind the band of the desired known material as the displacement agent is fed into column 2. The collection of the desired known material is then stopped as its concentration starts to drop and the concentration of the more strongly held component starts to rise, at a point determined by the purity chosen for the desired known material.

It is within the scope of the invention to stop the displacement step at the point where the collection of the desired known material is stopped, i.e., by stopping the flow of the displacement agent through column 2. However, it is preferred to continue the flow of displacement agent until the concentration of the displacement agent in the effluent is at least 95% of the concentration of the input. This minimizes other materials held on column 2 at the start of the next step of regeneration and minimizes the probability of problematic reactions in cyclic operation.

The Regeneration Step

Columns 1 and 2, after displacement and recovery of the desired known material from column 2, may be regenerated by any known means capable of removing all or substantially all, e.g., at least about 90% of the materials bound thereon by the just described process (although less materials may be removed from the packing material when economically feasible).

In accordance with a preferred embodiment of the invention, however, as shown in FIG. 3, the columns may be regenerated by continuing to pass through column 2 the same carrier (albeit without materials dissolved therein) as previously used to load the columns (to ensure solubility of the bound material in the eluting carrier). In some instances it may be economically preferred to change conditions to rapidly unload the column of displacing agent and other materials. For example the temperature could be increased in this regeneration step. Other examples would be changing the pH with an aqueous carrier, or changing to a different organic carrier to remove materials from the stationary phase using less carrier.

In any event, the flow of carrier effluent emerging from column 2 can then be monitored for the presence of displacement agent therein. When substantially all of the displacement agent has been removed from column 2, e.g., the effluent carrier from column 2 contains less than about 1% of the displacement agent concentration used in the displacement step, the flow of regenerating carrier fluid into column 2 may be shut off.

As noted in FIG. 3, the carrier effluent emerging from column 2 may be flowed into column 1 in a back flushing direction to remove the materials therein bound to the stationary phase packing in column 1. i.e. those materials originally separated from the known material by being more strongly bound to the packing material in column 1. By flowing the effluent carrier liquid from column 1 into column 2, the same liquid can be used to regenerate both columns at the same time. In such instance the effluent may be either monitored for the presence of displacement agent either as it flows out of column 2 or as the effluent flows out of column 1.

It will be further noted that by directing the flow of regenerating carrier fluid through column 1 in a countercurrent or back flushing direction, those materials most tightly bound to the stationary phase in column 1, i.e., those materials which were separated first from the carrier liquid and which, therefore, are bound to the stationary phase at the inlet of the column, will have the shortest distance to travel to be displaced from the column, i.e., will not be spread out across the entire column during the regeneration. Furthermore, when back flushing, the most tightly bound materials will be displaced by the next most tightly bound materials. Thus the efficiency of the regeneration of column 1 is increased by passing the regeneration carrier liquid through column 1 in a reverse flow direction. This is, of course, more important for column 1 than column 2 because the most strongly bound materials will be present in column 1, rather than column 2.

Turning now to FIG. 4, another embodiment of the regeneration portion of the invention is illustrated. In this embodiment, column 1 is back flushed, preferably during the displacement step being carried out in column 2 (which displacement step is also shown in FIG. 4 as well as previously in FIG. 2). This particular back flushing is preferably carried out using a different solvent than the original carrier solvent.

The purpose of this particular back flush (which may not always be needed), is to dissolve precipitates out of column 1 which may have deposited during the initial loading of column 1. Such precipitates may deposit in the stationary phase due to prior loading by another component also dissolved in the carrier fluid which rendered the precipitated component soluble in the carrier. That is, for example, the presence of component A dissolved in the carrier fluid may increase the solubility of component B in the carrier fluid. But if component A is more strongly bound to the stationary phase than component B, component B may precipitate as a solid in column 1 after component A is stripped out of the carrier fluid by the stationary phase. But in accordance with this aspect of the invention, if a solvent is selected which will dissolve this precipitate, eventual blocking of the column may be avoided by back flushing with such a solvent.

For cyclic operation at the completion of this regeneration step, the columns are returned to the conditions allowing the loading step to again proceed. The columns, if necessary, will also be returned to conditions allowing the original temperature and carrier compositions in the columns to be attained during the subsequent loading step.

Figure 5:
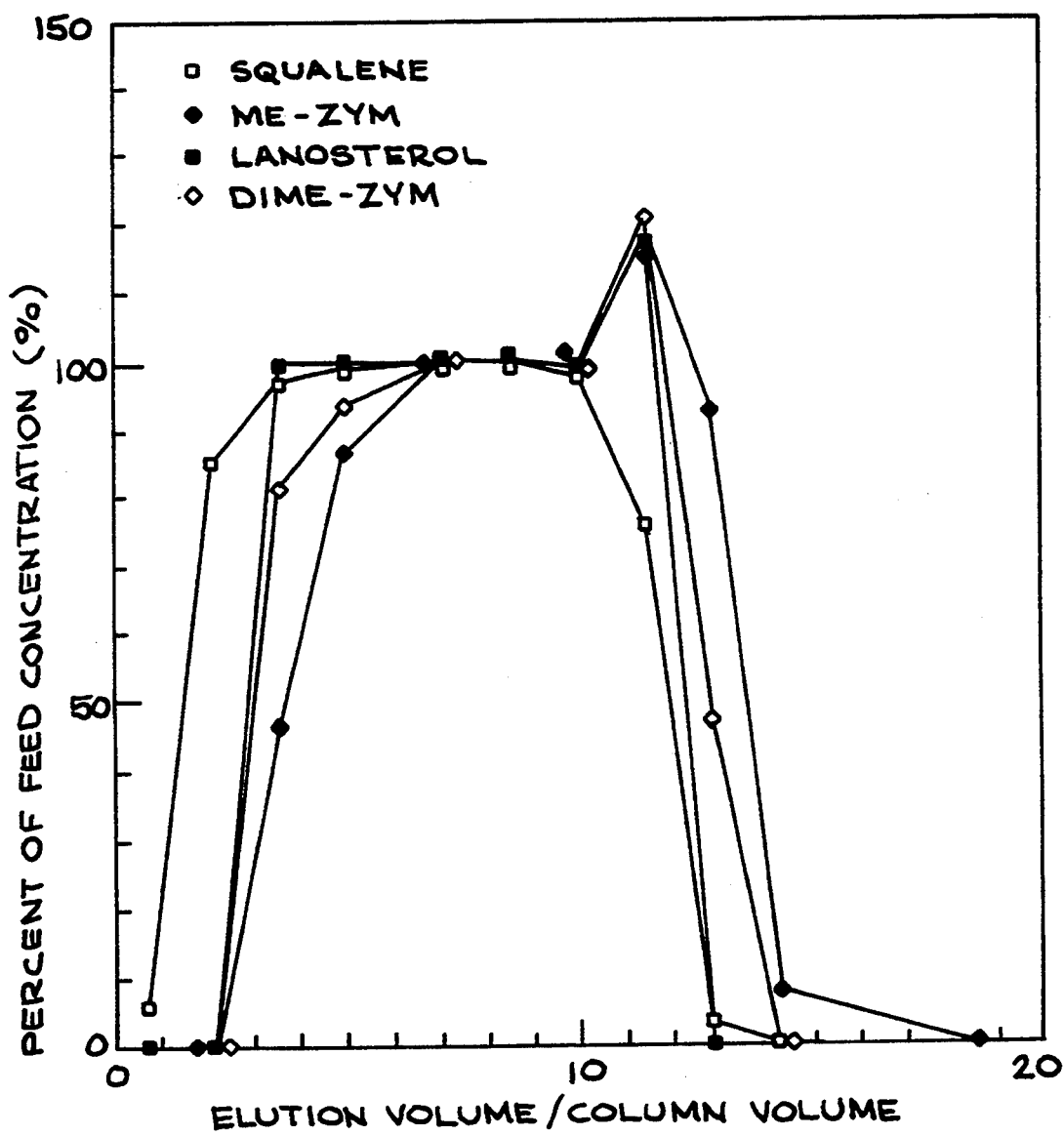
FIG. 5 is a graph showing the concentrations of the least strongly held components in the carrier exiting the first column.
Figure 6:
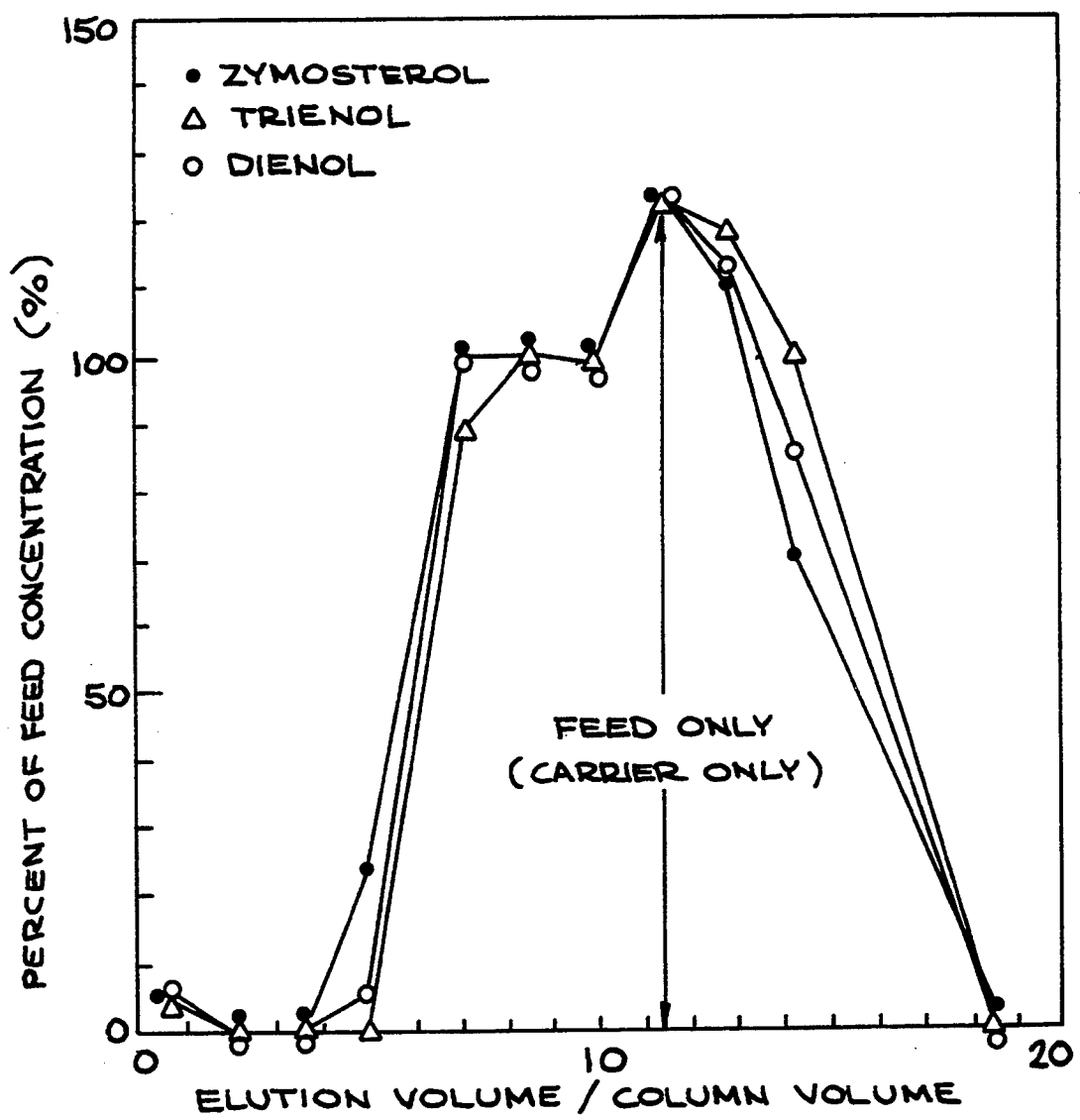
FIG. 6 is a graph showing the concentrations of the most strongly held components in the carrier exiting the first column. These materials include the desired known material, cholesta-5,7,24-triene-3-ol (trienol). Any materials more strongly held than trienol were not found in the exiting carrier and were assumed to be retained in the first column.

To further illustrate the practice of the invention, a 6 mm. diameter column was packed to a volume of 2 milliliters (ml) with silica gel with pores of nominal 150 Å diameter and a particle size range of 75–250 $\mu$m. A second column, of 1 cm. diameter, was packed to a volume of 35.6 ml with the same silica gel packing material, except that the packing material was loaded with 9 wt. % silver ions. A mixture containing cholesta-5,7,24-triene-3-ol (trienol) comprising the desired known organic material, together with a number or other steroid materials, was dissolved in a liquid carrier comprising 15 vol. % ethylacetate in heptane to form a 0.03 g/ml solution. A quantity of 20 ml of this solution was passed through the first column at 9 ml/min and into the second column. Then 20 ml of the same carrier (but without feed material therein) was pumped through the first column and into the second column thereby eluting material from the first column. The composition and concentrations of materials exiting column 1 with the eluting carrier are shown in FIGS. 5 and 6. The effluent from the first column was monitored by gas chromatography. The presence of trienol, the desired known organic material, had decreased to near zero in the effluent exiting the first column by the end of the 20 ml eluting step.

The desired known organic material (the trienol) had, at this point, been separated from those materials in the mixture more strongly bound to the stationary phase (with such more strongly held materials now bound to the stationary phase packing material in the first column) and the desired known material was now loaded on the stationary phase in the second column.

Figure 7:
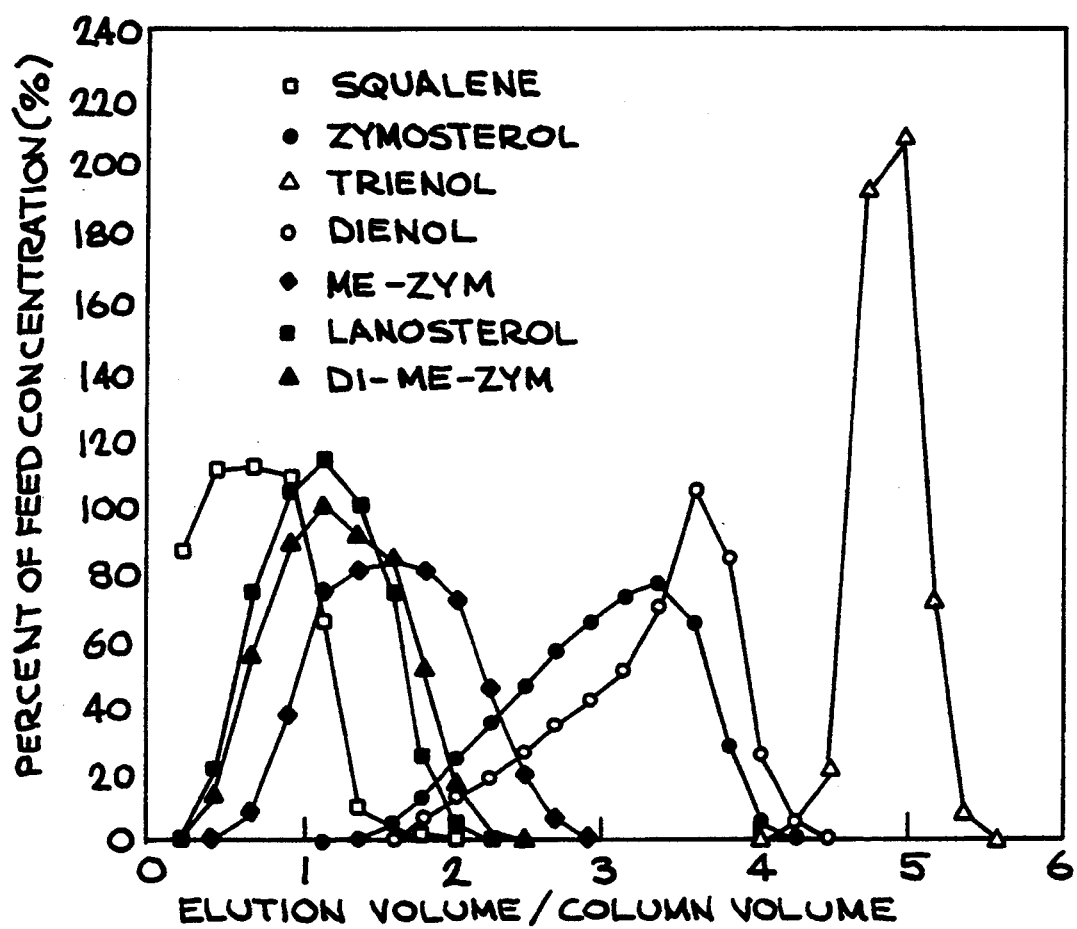
FIG. 7 is a graph showing the concentrations of materials displaced from the second column by the displacement agent for the same given mixture.

To displace the desired known organic material (trienol) from the stationary phase in the second column, in accordance with the second step of the process of the invention, a 0.01 gm/ml solution of the above carrier and 4-pentene-1-ol, a displacement agent known to be more strongly bound to the stationary phase packing material than trienol (the desired known organic material) was then fed into the second column at a rate of 4 ml/min. The effluent of this column was monitored for the appearance of the desired known organic material and this known material was then collected, while monitoring of the effluent continued either for a tapering off of the concentration of the desired known organic material, indicative that the dissolved displacement agent has displaced all of the known organic material in the column, or for the appearance of more than 1% of the inlet displacement agent concentration in the effluent. FIG. 7 shows the concentrations of the various materials displaced from column 2 by the displacement agent.

The known organic material, dissolved in the carrier, can be recovered by any conventional separation means such as evaporation, etc., with the liquid carrier then recovered, if desired, for carrying out the third step, i.e., regeneration of the stationary phase packing materials in the two columns.

The stationary phase packing materials in the respective columns was then regenerated by passing the same carrier fluid (but without any materials dissolved therein) through the second column. The regenerating carrier fluid effluent passed through the second column was then fed directly to the output port of the first column to thereby pass through the first column in a counter flow direction. The effluent from the first column was monitored until no further displacement agent, i.e., less than 1 percent of the initial concentration of displacement agent used in the displacement step, appeared in the carrier fluid emerging from the first column. The regeneration was then stopped. This occurred after about 300 ml of carrier was used.

Analysis of the solution of known organic material dissolved in the carrier fluid, or analysis of the known organic material after separation from the carrier, will show that the known organic material (trienol) was successfully separated from the other organic materials originally present in the solution introduced into the columns.

Thus the invention provides a practical displacement chromatography separation process wherein a desired known material may be separated from a mixture of materials wherein some of the materials in the mixture may be unidentified. By first removing from the mixture substantially all of the materials more strongly bound to the stationary phase than the known material which one desires to recover, one need only select a displacement agent more strongly bound to the stationary phase packing material than the known material, since one knows that all of the other materials left in the mixture after passing through the first column will be less strongly bound than the known material to be recovered. In the instance where a small amount of the first more strongly held material than the desired known material has also been passed to the second column, one then selects a displacement agent capable of also displacing this additional component as well, so that the displacement agent will, in either case, be capable of displacing all materials sorbed on the second column.

Having thus described the invention what is claimed is:

1. A process for separating a desired known material from a mixture of materials by displacement chromatography which comprises:
   a) passing said mixture, as a liquid, through a first column containing a stationary phase packing material, in a manner limiting the quantities of materials in said mixture, capable of being more strongly bound to said stationary phase than said desired known material, from passing from said first column to a second column while loading said desired known material, on the stationary phase packing material in said second column;
   b) stopping the flow of effluent from said first column into said second column; and
   c) then displacing from said second column all materials held thereon by passing through said second column a displacement agent more strongly bound to said stationary phase packing material in said second column than said materials thereon.

2. The process of claim 1 wherein said manner of limiting the quantities of material in said mixture, capable of being more strongly bound to said stationary phase than said desired known material, from passing from said first column to said second column comprises:
   a) monitoring the flow of such more strongly held materials in the effluent leaving said first column and entering said second column; and
   b) stopping said flow of effluent from entering said second column when the presence of such materials more strongly held than said desired known material is detected.

3. The process of claim 1 wherein said manner of limiting the quantifies of material in said mixture, capable of being more strongly bound to said stationary phase than said desired known material, from passing from said first column to said second column comprises: stopping the flow of said mixture through said first column at a predetermined point prior to detection, in the effluent from said first column, of said materials more strongly held than said desired known material.

4. The process of claim 1 including the further steps, after said step of stopping said flow of effluent from said first column into said second column, comprising:
   a) flowing an eluting carrier through said first column to elute from said first column said desired known material and materials less strongly held thereon; and
   b) flowing said eluted materials into said second column.

5. The process of claim 1 which further comprises displacing said desired known material from said second column by passing through said second column a displacement agent more strongly bound to said stationary phase packing material in said second column than said desired known material.

6. A process for separating a desired known material from a liquid mixture of materials by displacement chromatography which comprises:
   a) passing said liquid mixture through a first column containing a stationary phase packing material until substantially all of the materials in said mixture, capable of being more strongly bound to said stationary phase than said desired known material, have been separated from said mixture;
   b) passing the effluent from said first column through a second column to load said desired known material on the stationary phase packing material in said second column;
   c) stopping the flow of effluent from said first column into said second column; and
   d) then displacing said desired known material from said second column by passing through said second column a displacement agent more strongly bound to said stationary phase packing material in said second column than said desired known material.

7. The process of claim 6 wherein said effluent from said first column is monitored for the presence of materials more strongly held on said first column than said desired known material.

8. The process of claim 7 wherein said flow of effluent, from said first column into said second column, is shut off when said monitoring of said effluent from said first column reveals the presence in said effluent of materials more strongly held on said first column than said desired known material.

9. The process of claim 8 wherein said displacement agent selected to displace said desired known material from said second column is also selected to be capable of displacing from said second column at least the next more strongly held material than said desired known material in said mixture of materials to thereby provide for removal of all materials held on said second column when minor amounts of materials more strongly held than said desired known material pass into said second column before said effluent flow from said first column is shut off.

10. The process of claim 9 wherein the identity of such next more strongly held material is predetermined from a previous run of the same mixture under identical conditions through an identical column.

11. The process of claim 6 wherein said flow of effluent, from said first column into said second column, is stopped at a predetermined point prior to detection, in the effluent from said first column, of said materials more strongly held than said desired known material.

12. The process of claim 6 wherein the stationary phase packing material used in both column 1 and column 2 comprises the same material.

13. The process of claim 6 wherein the effluent from said second column is monitored, during said displacement step, for the presence of said displacement agent, indicating that substantially all of said desired known material has been displaced from said second column.

14. The process of claim 6 including the further step of regenerating said second column by passing carrier fluid through said column until the concentration of displacement agent in the effluent from said second column is less than about 1% of the initial concentration of said displacement agent fed into said second column.

15. The process of claim 14 including the further step of regenerating said first column by passing through said first column, in a forward direction, all of said effluent from said second column during said regeneration of said second column.

16. The process of claim 14 including the further step of regenerating said first column by passing through said first column, in a reverse direction, all of said effluent from said second column during said regeneration of said second column.

17. The process of claim 6 including the further step of removing precipitated material from said first column after said step of loading said first column with materials in said mixture more strongly bound that said particular material.

18. The process of claim 17 wherein said step of removing said precipitates from said first column further comprises passing through first column a liquid capable of dissolving said precipitated material therein.

19. The process of claim 18 wherein said liquid capable of dissolving said precipitated material in said first column is passed through said first column in a reverse direction.

20. A process for separating a desired known material from a liquid mixture of materials by displacement chromatography which comprises:
   a) passing said liquid mixture through a first column containing a stationary phase packing material until substantially all of the materials in said mixture, capable of being more strongly bound to said stationary phase than said desired known material, have been separated from said mixture and bound to said stationary phase material in said first column;
   b) passing into a second column also containing a stationary phase packing material the effluent collected from said first column to load said desired known material on said stationary phase in said second column;
   c) then displacing said desired known material from said second column by passing through said second column a displacement agent capable of displacing from said second column all materials bound to said stationary phase therein; and
   d) then regenerating said columns to remove materials still bound thereon.

21. The process of claim 20 wherein said process includes the further steps of:
   a) monitoring said effluent from said first column for the presence of materials in said effluent more strongly held by said stationary phase in said first column than said desired known material; and
   b) shutting off the flow of said effluent from said first column into said second column when said monitoring of said effluent from said first column reveals the presence of said more strongly held materials in said effluent.

22. The process of claim 20 wherein the displacement step of said process includes the further steps of:
   a) monitoring effluent flowing from said second column containing said desired known material for the presence of said displacement agent in said effluent; and
   b) shutting off said flow of effluent from said second column when said presence of said displacement agent is detected in said effluent from said second column.

23. The process of claim 22 wherein said flow of said effluent from said second column during said displacement step is shut off when said concentration of said displacement agent in said effluent reaches 5 ppm.

24. The process of claim 20 wherein said step of regenerating said columns further comprises passing carrier fluid through said second column until the concentration of said displacement agent in the effluent drops to below 1% of the original concentration of said displacement agent at the time of introduction of said displacement agent into said second column.

25. The process of claim 24 including the further step of regenerating said first column by passing through said first column, in a forward direction, all of said effluent from said second column during said regeneration of said second column.

26. The process of claim 24 including the further step of regenerating said first column by passing through said first column, in reverse direction, all of said effluent from said second column during said regeneration of said second column.

27. The process of claim 20 including the further step of removing precipitated material from said first column after said step of loading said first column with materials in said mixture more strongly bound that said known material.

28. The process of claim 27 wherein said step of removing said precipitates from said first column further comprises passing through first column, in a reverse direction, a liquid capable of dissolving said precipitated material therein.

29. A process for separating a desired known material from a liquid mixture of materials by displacement chromatography which comprises:
   a) passing said liquid mixture through a first column containing a stationary phase packing material;
   b) passing the effluent from said first column through a second column to load materials in said effluent on the stationary phase packing material in said second column;
   c) shutting off the flow of said liquid mixture through said first column and into said second column before materials more strongly held to said stationary phase in said first column than said desired known material appear in said effluent from said first column;
   d) then displacing from said first column and into said second column materials said desired known material and materials less strongly held therein than said desired known material by passing an eluting liquid through said first column;
   e) displacing said desired known material from said second column by passing through said second column a displacement agent more strongly bound to said stationary phase in said second column than said desired known material;
   f) monitoring the effluent from said second column for the presence of said displacement agent in said effluent from said second column;
   g) shutting off said flow of effluent from said second column when said presence of said displacement agent is detected in said effluent from said second column; and
   h) regenerating said columns to remove materials still bound thereon.

30. The process of claim 29 wherein said stationary phase in said first column is less strongly bound to said desired known material than said stationary phase in said second column.

31. The process of claim 29 wherein said elution step is carried out in said first column until the concentration of said desired known material in said effluent from said elution of said first column drops to about 1% of the concentration of said desired known material in said original liquid mixture.

* * * * *